Figure 1:
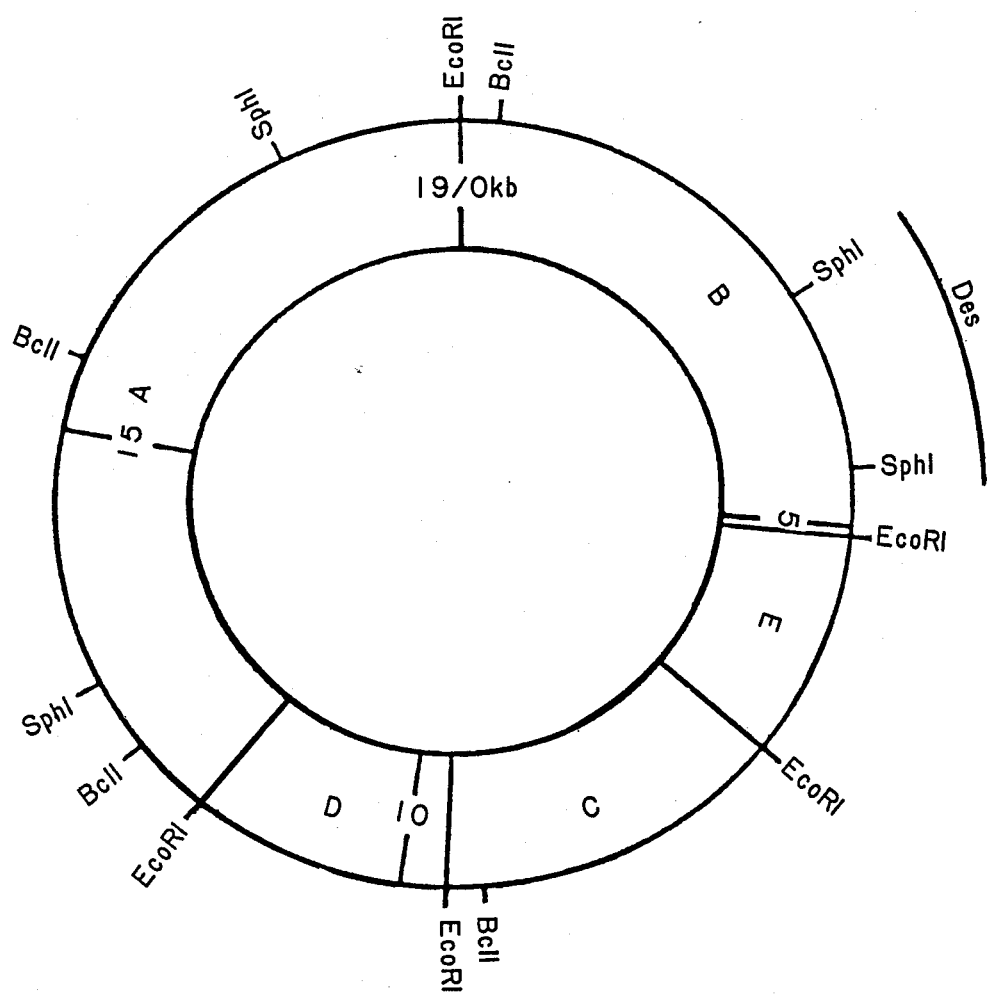

United States Patent [19]

Vandenbergh

[11] Patent Number: 4,822,740

[45] Date of Patent: Apr. 18, 1989

[54] BACTERIA FOR EXPRESSING A POLYSACCHARIDE DEPOLYMERASE CONTAINING A NOVEL RECOMBINANT PLASMID

[75] Inventor: Peter A. Vandenbergh, Sarasota, Fla.

[73] Assignee: Microlife Technics, Inc., Sarasota, Fla.

[21] Appl. No.: 784,769

[22] Filed: Oct. 7, 1985

[51] Int. Cl.[4] .................. C12N 9/24; C12N 9/36; C12N 1/20; C12N 15/00; C12R 1/18; A61K 37/54

[52] U.S. Cl. .................. 435/200; 435/206; 435/320; 435/847; 435/252.33; 935/27; 935/31; 935/73; 424/94.61

[58] Field of Search .................. 435/68, 253, 320, 206, 435/847, 200; 935/27, 31, 73; 424/94.61

[56] References Cited

PUBLICATIONS

Hartung, J. S., et al. (1984) Phytopathology 74(7), 838.
Ayers, A. R., et al, Appl. Environ, Microbial. 38: 659–666 (1979).
Adams, M. H., et al, Virology 2: 719–736 (1956).
Higashi, S., et al, J. Gen. Appl. Microbiol. 24:143–153 (1978).
Hartung, J. S., et al., Phytopathology 72: 945 (1982).
Boliver, et al., Methods of Enzymol 68: 245–267 (1979).
Winter, R. B., et al., Cell 33: 877–885 (1983).
Vievia, J., et al., Gene 19: 259–268 (1982).
DeBoer, H. A., et al., P.N.A.S. 80: 21–25 (1983).
Davis, R. W., et al., A Manual for Genetic Engineering: Adv. Bacter. Genetics. Cold Spring Harbor Lab., Cold Spring Harbor, N.Y. (1980).
Yamamoto, K. R., et al., Virology 40: 734–744 (1970).
Vandenbergh, P. A., et al., J. Dent. Res. 61:497–501 (1982).
Fairbridge, R. A., et al., Biochem. J. 49: 423–427 (1951).
Liu, P. V., et al., J. Infect. Dis 108: 218–228 (1961).
Koch, A., et al., Anal. Biochem. 44: 239–245 (1971).
Amann, E., et al., Gene 25: 167–178 (1983).
Fuller, F., Gene 19: 43–54 (1982).

*Primary Examiner*—Thomas G. Wiseman
*Assistant Examiner*—Charles L. Patterson, Jr.
*Attorney, Agent, or Firm*—Ian C. McLeod

[57] ABSTRACT

A segment of a bacteriophage encoding for a polysaccharide depolymerase which has been cloned and expressed in *Escherichia coli* is described. In particular, bacteriophage ERA103 was found to consist of five EcoRI fragments labeled: A, 7.5-kb; B, 5.0-kb; C, 2.7-kb; D, 2.1-kb and E, 1.8-kb. Fragment B encodes for the depolymerase and was cloned into the positive-selection vector pOP203($A_2^+$), pBR322 and the expression vector pKK223-3. The depolymerase is applied to rosaceous plants to prevent Fireblight caused by *Erwinia amylovora* by depolymerizing a polysaccharide produced by this bacteria.

27 Claims, 1 Drawing Sheet

BACTERIA FOR EXPRESSING A POLYSACCHARIDE DEPOLYMERASE CONTAINING A NOVEL RECOMBINANT PLASMID

BACKGROUND OF THE INVENTION

1. Field of the Invention

The present invention relates to recombinant plasmids and to bacteria containing the recombinant plasmids which produce polysaccharide depolymerase, wherein the recombinant plasmid contains a DNA segment of a bacteriophage for *Erwinia amylovora*. In particular the present invention relates to *Escherichia coli* containing a recombinant plasmid with a DNA segment of phage ERA103 which expresses a depolymerase.

2. Prior Art

*Erwinia amylovora* is recognized as the causitive agent of fireblight in rosaceous plants (Ayers, A. R., et al., Appl. Environ. Microbiol. 38: 659–666 (1979)). The pathogenic strains of this bacteria have been demonstrated to produce a polysaccharide capsule which has been implicated in xylem vessel occlusion and plasmolysis of xylem parenchymal cells, which are symptomatic of the disease. U.S. patent application Ser. No. 662,056, filed Oct. 18, 1984 now U.S. Pat. No. 4,678,750 describes the use of a bacteriophage induced depolymerase from *Erwinia amylovora* for the treatment of this disease.

Bacteriophage encoded polysaccharide depolymerases have been described for many bacterial genera (Adams, M. H., et al., Virology 2: 719–736 (1956) and Higashi, S., et al., J. Gen. Appl. Microbiol. 24: 143–153 (1978)). Bacteriophage PEal (h) has been shown to degrade to the polysaccharide capsule of *Erwinia amylovora* (Hartung, J. S., et al., Phytopathology 72: 945 (1982)). Bacteriophage ERA103 has been found to infect the plant pathogen *E. amylovora* NCPPB595 and produce a depolymerase that degrades the polysaccharide capsule of this bacteria. The problem is that it is difficult and expensive to isolate significant amounts of the depolymerase by induction with the bacteriophage.

Much more of the depolymerase might be obtained if it was possible to clone a segment of the phage DNA encoding for the depolymerase into a vector plasmid. It was uncertain whether the depolymerase could be produced without the presence of the host *Erwinia amylovora* or whether the genes responsible for encoding the depolymerase could be cloned into a recombinant plasmid.

Objects

It is therefore an object of the present invention to provide a recombinant plasmid in a bacteria which encodes for the expression of a depolymerase. Further the present invention relates to a recombinant plasmid including a segment of a bacteriophage which infects *Erwinia amylovora* and which encodes for the depolymerase. In particular it is an object of the present invention to provide a recombinant plasmid including a segment of bacteriophage ERA 103 which encodes for the expression of the depolymerase in *E. coli*. Finally, it is an object of the present invention to provide a method for producing the depolymerase using the recombinant plasmid which is simple and economical. These and other objects will become increasingly apparent by reference to the following description and the drawings.

IN THE DRAWINGS

FIG. 1 is a restriction map of bacteriophage ERA103 DNA wherein fragments have been lettered in order of decreasing size. Dep represents the fragment expressing the depolymerase activity.

FIG. 2 is an agarose gel electrophoresis of DNA preparations purified with cesium chloride-ethidium bromide and digested with EcoRI as the restriction endonuclease enzyme. The agarose concentration was 0.7%, and migration was from top to bottom. The contents of lanes are as follows: (A) EcoRI digested pSRQ51; (B) EcoRI digested pSRQ52; (C) EcoRI digested pSRQ53; (D) EcoRI digested pSRQ54; (E) EcoRI digested pSRQ55; (F) EcoRI digested bacteriophage ERA103; (G) EcoRI digested pOP203($A_2^+$).

GENERAL DESCRIPTION

The present invention relates to a recombinant plasmid which can express a polysaccharide depolymerase in bacteria containing the plasmid which comprises: a linear segment from a bacteriophage which infects *Erwinia amylovora* to produce the depolymerase and which codes for the depolymerase; and a transformable vector plasmid segment ligated to the linear segment to provide the recombinant plasmid.

Further the present invention relates to a bacteria which expresses a polysaccharide depolymerase because of a resident recombinant plasmid wherein the recombinant plasmid comprises: a linear segment from a bacteriophage which infects *Erwinia amylovora* to produce the depolymerase and which codes for the depolymerase; and a transformable vector plasmid segment ligated to the linear segment to provide the recombinant plasmid.

Finally the present invention relates to a method for producing a polysaccharide depolymerase which comprises: providing a bacteria for expressing the polysaccharide depolymerase containing a resident recombinant plasmid with a linear segment from a bacteriophage which infects *Erwinia amylovora* to produce the depolymerase and which codes for the depolymerase and with a transformable vector plasmid segment which has been ligated to the linear segment to provide the recombinant plasmid; growing the bacteria in a growth medium to produce the depolymerase; and removing the depolymerase from the bacteria and growth medium.

The preferred bacteriophage is ERA 103; however other bacteriophages which induce the depolymerase in *Erwinia amylovora* which could be used are ERA 225 and ERA 101 which are freely available from the University of Nebraska, Dr. Anne K. Vidaver, Department of Plant Pathology.

The following specific description includes the mapping of the bacteriophage genome and the cloning of a fragment (B) from ERA103 into (1) pBR322 (Bolivar, et al., Methods of Enzymol 68: 245–267 (1979)), (2) the positive-selection vector pOP203($A_2^+$) (Winter, R. B., et al., Cell 33: 877–885 (1983)), or (3) the expression vector pKK223-3 (Vievia, J., et al., Gene 19: 259–268 (1982)), as the plasmids and expression of the depolymerase in *Escherichia coli*. The positive selection vector pOP203($A_2^+$) contains genes that are lethal to the bacterial host. Therefore, when DNA fragments are inserted into the unique restriction sites, expression of genes deleterious to the host are suppressed. The expression vector pKK223-3 was developed for high level regulated expression of protein products in *E. coli*. This plasmid contains the strong trp-lac (tac) promoter which facilitates the expression of cloned genes during induction. The procedure is generally described by DeBoer, H. A., et al., P.N.A.S. 80: 21–25 (1983).

SPECIFIC DESCRIPTION

Materials and Methods

Bacterial strains and media. Bacterial strains used or constructed in this invention are presented in Table 1.

TABLE 1

Bacterial Strains and Plasmids

| | Remarks | Reference |
|---|---|---|
| Strain | | |
| Bacteria | | |
| *E. coli* | | |
| HB101 | lacI$^{qa}$ | (1) |
| HB101(pOP203A$_2$+) | contains positive selection vector | (1) |
| HB101(pBR322) | contains plasmid pBR322 | (4) |
| JM105 | lacI$^b$ | (3) |
| JM105(pKK223-3) | contains expression vector | (2) |
| Plasmids | | |
| pOP203(A$_2$+) | lac$^b$ A$_2{}^c$ tet$^d$ | (1) |
| pBR322 | bla$^3$ tet | (4) |
| pKK223-3 | bla tet tac$^f$ | (4) |
| pSRQ51 | phage fragment A in pOP203(A$_2$+)EcoRI site | present invention |
| pSRQ52 | phage fragment B in pOP203(A$_2$+) EcoRI site | NRRL-B-15989 |
| pSRQ53 | phage fragment C in pOP203(A$_2$+) EcoRI site | present invention |
| pSRQ54 | phage fragment D in pOP203(A$_2$+) EcoRI site | present invention |
| pSRQ55 | phage fragment E in pOP203(A$_2$+) EcoRI site | present invention |
| pSRQ56 | phage fragment B in pBR322 EcoRI site | NRRL-B-15990 |
| pSRQ57 | phage fragment B in pKK223-3 EcoRI site | NRRL-B-15991 |
| pSRQ58 | SphI segment of the B fragment in pBR322 SphI site | present invention |

$^a$hyperlactose repressor-producing mutation carried by F'lac exogenate.
$^b$lactose promoter/operator.
$^c$maturation protein gene of the RNA bacteriophage Qbeta.
$^d$tetracycline resistance.
$^e$ampicillin resistance.
$^f$trp-lac promoter.
(1) Winter, R. B., et al. Cell 33: 877–885 (1983).
(2) DeBoer, H. A., et al. P.N.A.S. 80: 21–25 (1983)
(3) Vievia, J., et al. Gene 19: 259–268 (1982).
(4) Bolivar, F., et al., Methods Enzymol 68: 245–267 (1979).

*E. coli* strains were grown in L broth (Davis, R. W., et al., A manual for genetic engineering: advanced bacterial genetics. Cold spring Harbor Laboratory, Cold Spring Harbor, N. Y. (1980)). Tetracycline (Sigma Chemical Co., St. Louis, Mo.) was added to media at a concentration of 10 micrograms/ml. Carbenicillin (United States Biochemical Corporation, Cleveland, OH.) was added to media at a concentration of 50 micrograms/ml. Isopropyl B-D-thiogalactoside (IPTG; Sigma) was added to the media for a final concentration of 1.0 mM where indicated.

Bacteriophage preparation

High titer stocks of bacteriophage ERA103 ($10^{11}$ to $10^{12}$ PFU/ml) were developed as previously described (Yamamoto, K. R., et al., Virology 40: 734–744 (1970)).

Plasmid and bacteriophage DNA isolation

Plasmid DNA was isolated from *E. coli* by a method previously described in the literature (Vandenbergh, P. A., et al., J. Dent. Res. 61: 497–501 (1982)). Polyethylene glycol (PEG) precipitated high titer phage preparations were centrifuged in cesium chloride-ethidium bromide gradients. The cesium chloride purified bacteriophage DNA was dialyzed overnight in 4.0 l of 0.01M tris (hydroxymethyl) aminomethane-hydrochloride (pH 8.0) containing 0.001M ethylenediaminetetracetic acid. Subsequently, the bacteriophage DNA preparation was extracted twice with saturated phenol and ethanol precipitated.

Bacterial transformations

*E. coli* was transformed by the CaCl$_2$-heat shock method (Davis, R. W., et al. A manual for genetic engineering: advanced bacterial genetics. Cold Spring Harbor Laboratory, Cold Spring Harbor, N.Y. (1980)), with cells harvested at an absorbance of 0.6 (600 nm).

Restriction endonuclease digestion and ligation

Restriction endonucleases and T4 DNA ligase (Bethesda Research Laboratories, Bethesda, MD.) were used in the buffers and under the conditions recommended by the supplier.

Construction and screening of clones

Bacteriophage ERA103 DNA was digested with EcoRI and ligated with pOP203(A$_2$+) or pBR322 vectors cut to completion with EcoRI. The ligation mixture contained approximately a 1:2 ratio of vector DNA to bacteriophage DNA. Bacteriophage ERA103 DNA was digested with EcoRI and ligated with pKK223-3 vector cut to completion with EcoRI. The ligation mixture contained approximately a 1:10 ratio of vector DNA to bacteriophage DNA. Ligation was performed at 17° C. for 18 hours. The ligation procedure uses DNA T4 ligase as described by Bolivar et al (1979).

Determination of depolymerase activity

Bacterial cultures were grown overnight in L broth at 37° C. supplemented with either tetracycline at a concentration of 10 micrograms/ml, or carbenicillin at a concentration of 50 micrograms/ml depending on the vector utilized. This culture was then deluted 1:100 into 250 ml of similar media with cells harvested at an absorbance of 0.9 (600 nm). All subsequent fractionation steps were performed at 4° C. The cells were then centrifuged at 8,000 xg for 30 min. The pellet was then suspended in sterile distilled water and centrifuged at 8,000 xg for 30 minutes. The washed pellet was then resuspended in 10 ml of 0.01M citrate buffer (pH 6.0) containing 0.01M 2-mercaptoethanol. Cell-free extracts (CFE) were prepared by passage of washed cell suspensions through a French Press at 16,000 p.s.i., three times. The resultant CFE was then centrifuged at 27,000 xg for 30 minutes to remove whole cells and cell debris. Ammonium sulfate was added slowly to the supernatant to give a final concentration of 45% saturation and precipitated for 18 hours. The ammonium sulfate precipitate was centrifuged at 27,000 xg for 30 minute and dialyzed overnight against buffer. Depolymerase activity was assayed by following the release of galactose from the polysaccharide substrate by the method of Fairbridge et al (Fairbridge, R. A., et al., Biochem. J. 49: 423–427 (1951)). Polysaccharide was prepared from uninfected cultures of *E. amylovora* NCPPB595 cultivated on sheets of cellophane overlaying tryptic soy agar, as described by Liu et al (Liu, P. V., et al., J. Infect. Dis 108: 218–228 (1961)).

One unit of enzyme is the amount of enzyme to produce 1 micromole of galactose equivalent per minute under standard assay conditions. Protein concentrations were determined by the method of Koch and Putnam (Koch, A., et al., Anal. Bicohem. 44: 239–245 (1971)).

Induction Studies

Bacterial culture were grown overnight in L broth at 37° C. supplemented with the appropriate antibiotic. This culture was then diluted 1:100 into 250 ml of similar media until the cells reached an absorbance of 0.7 (600 nm). IPTG was added to a final concentration of 1 mM, and incubated until an absorbance of 0.9 (600 nm) was obtained. The cultures were then processed as described in the previous section.

Preparation of Depolymerase

FIG. 1 which is a restriction map depicts the relative positions of various restrictions endonuclease recognition sites on phage ERA103 DNA obtained using a combination of the following procedures: (i) analysis of DNA fragments obtained after digestion with two enzymes; (ii) analysis of E. coli plasmids containing phage ERA103 EcoR1 fragments. DNA from phage ERA103 was cleaved by EcoR1 into five distinct fragments labeled: A, 7.5-kb; B, 5.0-kb; C, 2.7-kb; D, 2.1-kb and E, 1.8-kb. Several restriction enzymes: BamHI, BstEII, ClaI, HindIII, KpnI, PstI, SalI and SstI, did not cleave the phage DNA.

Figure 2:
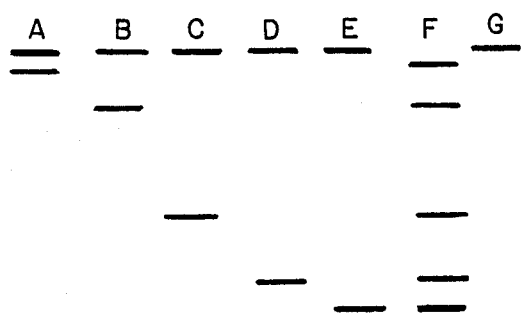

The plasmid pOP203($A_2^+$) contains the lac promoter-operator fused to the Q beta phage maturation gene. Positive selection results when only survivors with inserts in the $A_2$ gene grow in the presence of IPTG. Since the vector has several unique restriction sites, including EcoRI, this vector was used. Colonies were then screened for the presence of plasmid DNA containing the five EcoRI phage fragments. All five EcoRI fragments were cloned into pOP203($A_2^+$) (FIG. 2). The plasmid containing strains were grown in 250 ml of L broth containing tetracycline at 10 micrograms/ml. Enzyme assays in triplicate of CFE of each cloned fragment demonstrated that enzyme activity was associated with the B fragment which is 5.0-kb, and contained in pSRQ52. Depolymerase activity was always associated with the supernatants of the CFE and not demonstrated in the pellets.

Mapping data revealed the presence of SphI sites in the phage ERA103 DNA. The vector pBR322 was utilized because of the insertional inactivation of tetracycline resistance in the SphI site of this vector. Transformants that were resistant to carbenicillin and sensitive to tetracycline were screened for plasmids and depolymerase activity. An E. coli strain containing the plasmid pSRQ58, a 1.5-kb portion of the B fragment demonstrated depolymerase activity.

Additional cloning experiments utilized the expression vector pKK223-3. The B fragment was cloned in the EcoRI site of this plasmid.

Expression of the enzyme was examined utilizing various E. coli strains containing the cloned depolymerase fragment as shown in Table 2.

TABLE 2

| Depolymerase activity by E. coli HB101 containing various plasmids. | | |
|---|---|---|
| Plasmid | Growth Conditions | Enzyme sp. act.[a] |
| None | Uninduced | 0[b] |
| pBR322 | Uninduced | 0 |
| pSRQ56 | Uninduced | 27.1 |
| pSRQ58 | Uninduced | 39.0 |
| pOP203($A_2^+$) | Uninduced | 0 |
| pOP203($A_2^+$) | Induced | 0 |
| pSRQ52 | Uninduced | 28.0 |
| pSRQ52 | Induced | 34.0 |
| pKK223-3 | Uninduced | 0 |
| pKK223-3 | Induced | 0 |
| pSRQ57 | Uninduced | 34.0 |

TABLE 2-continued

| Depolymerase activity by E. coli HB101 containing various plasmids. | | |
|---|---|---|
| Plasmid | Growth Conditions | Enzyme sp. act.[a] |
| pSRQ57 | Induced | 47.2 |

[a]Specific activities are expressed in micromole of galactose equivalent per minute per milligram of protein under standard assay conditions.
[b]A measurement of zero implies activity of <0.05.

The E. coli strains containing pSRQ57 or pSRQ52 were grown and induced with IPTG or uninduced. The E. coli strains containing pSRQ56 or pSRQ58 were also grown and compared to the above E. coli strains. The CFE supernatants were precipitated with ammonium sulfate and dialyzed against buffer. All of the ammonium sulfate precipitates were standardized to equivalent protein concentrations and assayed for depolymerase in triplicate. The E. coli strains containing plasmids with the tac promoter produced about twenty additional depolymerase units upon induction. Strains containing plasmids with only the lac promoter produced about seven additional units when induced. Thus 13.2 and 6 additional units of specific activity are shown in Table 2 for induced versus non-induced pSRQ57 and pSRQ52, respectively. Table 2 demonstrates that the gene coding for the depolymerase from the bacteriophage ERA103 and related bacteriophages can be cloned into pBR322, pOP203($A_2^+$), pKK223-3 and expressed in E. coli. It can also be expressed with other vectors and bacteria as will be obvious to those skilled in the art.

The physical map of ERA103 in FIG. 1 includes the positions for cleavage sites of three restriction enzymes. Enzyme assays conducted on the cell free extract (CFE) supernatants of the five cloned EcoRI fragments of bacteriophage DNA demonstrated that the depolymerase activity was associated with the 5.0-kb B fragment. Subsequent subcloning utilizing pBR322, associated the activity within a 1.5-kb SphI fragment. When the depolymerase activity of entire cloned B fragment in either pBR322 or uninduced pOP203($A_2^+$) was compared to the activity of the subcloned SphI fragment, the activity was 69% greater in the subcloned SphI fragment. Induction utilizing the entire B fragment cloned in the expression vector pKK223-3 demonstrated a 44% increase in enzymatic activity compared to the same fragment cloned into pBR322. Use of the positive selection vector pOP203($A_2^+$) resulted in a 74% increase in activity compared to pBR322.

The plasmid pOP203($A_2^+$) was derived from pOP203-3, a pMB9 plasmid carrying the lac UV5 promoter (Fuller, F., Gene 19: 43–54 (1982)). The expression vector pKK223-3 contains the lacUV5 promoter and the trp promoter, i.e. tac (Amann, E., et al., Gene 25: 167–178 (1983)). The plasmid pBR322 does not have a lac promoter. Enzymatic assays indicated that the expression level varied with the promoter utilized.

The polysaccharide depolymerase is a replacement for antibiotic therapy in the control of E. amylovora, the causitive agent of Fireblight. Plants were treated with the depolymerase alone or as shown in U.S. patent application Ser. No. 662,056, filed Oct. 18, 1984 now U.S. Pat. No. 4,678,750. The depolymerase can be combined with various leaf wetting agents or polymeric adhesives to cause the enzyme to adhere to the plant.

The foregoing specific description is only illustrative of the present invention and it is intended that the present invention be limited only by the hereinafter appended claims.

I claim:

1. A recombinant plasmid which can express a polysaccharide depolymerase in bacteria containing the plasmid which comprises:

(a) a linear segment from bacteriophage ERA 103 deposited as ATCC 39824 Bl which infects Erwinia amylovora to produce the depolymerase and which segment codes for the production of the depolymerase; and (b) a transformable vector plasmid segment ligated to the linear segment to provide the recombinant plasmid wherein the recombinant plasmid is stable in the bacteria so as to express the depolymerase.

2. The recombinant plasmid of claim 1 as carried in *E. coli* NRRL-B-15989.

3. The recombinant plasmid of claim 1 as carried in *E. coli* NRRL-B-15990.

4. The recombinant plasmid of claim 1 as carried in *E. coli* NRRL-B-15991.

5. The recombinant plasmid of claim 1 wherein the linear segment from ERA 103 is cleaved by endonuclease EcorI, SphI, or EcoI and then SphI and the vector plasmid is selected from pOP203($A_2$+), pBR322 and pKK223-3 cleaved by EcoRI and then ligated to the linear segment to provide the recombinant plasmid.

6. The recombinant plasmid of claim 1 wherein the bacteria is *E. coli.*

7. The plasmid of claim 1 wherein the vector plasmid and linear segment have been cleaved by EcoRI and ligated.

8. The plasmid of claim 1 wherein the bacteriophage lyses *Erwinia amylovora* and wherein the polysaccharide depolymerase degrades a polysaccharide capsule around the *Erwinia amylovora.*

9. The plasmid of claim 8 wherein the *Erwinia amylovora* is deposited as ATCC 39824.

10. A bacteria which expresses a polysaccharide depolymerase because of a resident recombinant plasmid wherein the recombinant plasmid comprises:

(a) a linear segment from bacteriophage ERA 103 deposited as ATCC 39824 Bl which infects *Erwinia amylovora* to produce the depolymerase and which segment codes for the production of the depolymerase; and (b) a transformable vector plasmid segment ligated to the linear segment to provide the recombinant plasmid wherein the recombinant plasmid is stable in the bacteria so as to express the depolymerase.

11. The bacteria of claim 10 containing the recombinant plasmid as carried in *Escherichia coli* NRRL-B-15990.

12. The bacteria of claim 10 containing the recombinant plasmid carried in *Escherichia coli* NRRL-B-15991.

13. The bacteria of claim 10 containing the recombinant plasmid as carried in *E. coli* NRRL-B-15989.

14. The bacteria of claim 10 wherein the linear segment from ERA 103 is cleaved by endonuclease EcoRI, SpHI or EcoRI and then SphI and the vector plasmid is selected from pOP203 ($A_2$+), pBR322 and pKK223-3 cleaved by EcoRI and then ligated to the linear segment to provide the recombinant plasmid.

15. The bacteria of claim 10 which is a strain of *Escherichia coli.*

16. The bacteria of claim 10 wherein the vector plasmid and the linear segment have been cleaved by EcoRI and ligated.

17. The bacteria of claim 10 wherein the bacteriophage lyses *Erwinia amylovora* and wherein the polysaccharide depolymerase degrades a polysaccharide capsule around the *Erwinia amylovora.*

18. The bacteria of claim 17 wherein the *Erwinia amylovora* is ATCC 39824.

19. A method for producing a polysaccharide depolymerase which comprises:

(a) providing a bacteria for expressing the polysaccharide depolymerase containing a resident recombinant plasmid with a linear segment from bacteriophage ERA 103 deposited as ATCC 39824 Bl which infects Erwinia amylovora to produce the depolymerase and which segment codes for the production of the depolymerase and with a transformable vector plasmid segment which has been ligated to the linear segment to provide the recombinant plasmid wherein the recombinant plasmid is stable in the bacteria so as to express the depolymerase;

(b) growing the bacterial in a growth medium to produce the depolymerase; and (c) removing the depolymerase from the bacteria and growth medium.

20. The method of claim 19 wherein cells of the bacteria are ruptured and the depolymerase is removed from the ruptured cells.

21. The method of claim 19 wherein the bacteria is *Escheichia coli.*

22. The method of claim 19 wherein the recombinant plasmid is carried in *Escherichia coli* NRRL-B-15989.

23. The method of claim 19 wherein the recombinant plasmid is carried in *Escherichia coli* NRRL-B-15990.

24. The method of claim 19, wherein the recombinant plasmid is carried in *E. coli* NRRL-B-15991.

25. The method of claim 19 wherein the linear segment from ERA 103 ATCC 39824 Bl is cleaved by endonuclease EcoRI, SphI or EcoRI and then SphI and the vector plasmid is selected from pOP203 ($A_2$+), pBR322 and pKK223-3 cleaved by EcoRI and then ligated to provide the recombinant plasmid.

26. The method of claim 19 wherein the bacteriophage lyses *Erwinia amylovora* and wherein the depolymerase degrades a polysaccharide capsule of the *Erwinia amylovora.*

27. The method of claim 26 wherein the *Erwinia amylovora* is ATCC 39824.

* * * * *